(12) United States Patent
Niederbacher (10) Patent No.: US 9,540,605 B2
(45) Date of Patent: Jan. 10, 2017

(54) BIOGAS PLANT

(71) Applicant: Michael Niederbacher, Bruneck (IT)

(72) Inventor: Michael Niederbacher, Bruneck (IT)

( * ) Notice: Subject to any disclaimer, the term of this patent is extended or adjusted under 35 U.S.C. 154(b) by 164 days.

(21) Appl. No.: 14/417,342

(22) PCT Filed: Jul. 11, 2013

(86) PCT No.: PCT/EP2013/002042
§ 371 (c)(1),
(2) Date: May 11, 2015

(87) PCT Pub. No.: WO2014/015949
PCT Pub. Date: Jan. 30, 2014

(65) Prior Publication Data
US 2015/0259636 A1    Sep. 17, 2015

(30) Foreign Application Priority Data
Jul. 26, 2012 (EP) .................................. 12005444

(51) Int. Cl.
*C12M 1/107* (2006.01)
*B01F 7/00* (2006.01)
(Continued)

(52) U.S. Cl.
CPC ............ *C12M 21/04* (2013.01); *B01F 7/0095* (2013.01); *B01F 7/00741* (2013.01);
(Continued)

(58) Field of Classification Search
CPC ....... C12M 21/04; C12M 23/00; C12M 23/38; C12M 27/06; C12M 23/36; C12M 23/48; C12M 39/00; C12P 5/023; B01F 7/02; B01F 7/00733; F16M 13/022; Y02E 50/343; Y10T 29/49718; Y10T 37/0441; Y10T 137/7043
See application file for complete search history.

(56) References Cited

U.S. PATENT DOCUMENTS 4,559,840 A    12/1985    Sasaki
5,269,603 A *  12/1993    Lisi ..................... B01F 7/00733
                                                       366/261
(Continued)

FOREIGN PATENT DOCUMENTS

AU        622391 B3    2/1992
DE       7934124 U1    3/1980
(Continued)

*Primary Examiner* — Gautam Prakash
(74) *Attorney, Agent, or Firm* — Laurence A. Greenberg; Werner H. Stemer; Ralph E. Locher (57) ABSTRACT

A biogas plant contains a fermenter vessel, in which an assembly support is mounted, preferably vertically oriented. An assembly, in particular a submersible motor driven stirrer, is retained by a height adjustment device so as to be vertically adjustable on the assembly support. Accordingly, the height adjustment device is formed by a belt drive of which a traction device is guided around at least two deflecting elements spaced apart from one another in the longitudinal direction of the assembly support. At least one of the deflecting elements can be driven in rotation by a driving device and the assembly is coupled to the traction device in such a way that when the deflecting element is rotationally actuated in a first direction the assembly is raised and when the deflecting element is rotationally actuated in a second, opposite direction, the assembly is lowered.

12 Claims, 5 Drawing Sheets

(51) Int. Cl.
*B01F 7/02* (2006.01)
*C12M 3/00* (2006.01)
*C12M 1/06* (2006.01)
*F16M 13/02* (2006.01)

(52) U.S. Cl.
CPC .......... *B01F 7/00941* (2013.01); *B01F 7/02* (2013.01); *C12M 23/48* (2013.01); *C12M 27/06* (2013.01); *F16M 13/022* (2013.01); *Y02E 50/343* (2013.01)

(56) References Cited

U.S. PATENT DOCUMENTS

| | | | | |
|---|---|---|---|---|
| 2009/0218279 | A1* | 9/2009 | Eichler | B03D 1/02 |
| | | | | 210/603 |
| 2010/0096343 | A1* | 4/2010 | Hoefken | B01F 7/0005 |
| | | | | 210/787 |
| 2012/0009664 | A1* | 1/2012 | Buerger | C12M 21/04 |
| | | | | 435/286.5 |
| 2012/0164720 | A1* | 6/2012 | Bierer | B01F 7/00733 |
| | | | | 435/289.1 |

FOREIGN PATENT DOCUMENTS

| | | |
|---|---|---|
| DE | 3738390 A1 | 6/1989 |
| EP | 0894525 A2 | 2/1999 |

* cited by examiner

BIOGAS PLANT

BACKGROUND OF THE INVENTION

Field of the Invention

The invention relates to a biogas plant according to the preamble of the main claim.

Biogas plants having a fermenter tank, in which an assembly carrier is mounted, preferably oriented vertically, are generally known. An assembly, in particular a submersible motor-driven agitator, is usually held on the assembly carrier in a height-adjustable manner by means of a height adjustment device.

A height adjustment device for a submersible motor-driven agitator is already known from EP 0 894 525 B1, the height adjustment device being designed here as a rope winch which has a rope drum connected firmly to the assembly carrier and having a horizontal rope drum shaft. Further, a rope which, on the one hand, is connected to the assembly and, on the other hand, can be wound onto the rope drum is provided, the rope drum being arranged inside the fermenter tank, so that there is no need for a gastight rope leadthrough through a tank wall. The rope drum is assigned a rope drum drive which can be actuated by means of an actuation device arranged outside the tank.

A rope winch of this type as a height adjustment device has a series of disadvantages: thus, on the one hand, the disadvantage that the rope is guided and accommodated in the fermenter tank containing substances and liquids to be fermented and also gases which constitute a highly corrosive medium for the rope which is usually produced as a steel rope. Moreover, the risk of corrosion is further increased in that, when the rope is wound onto the rope drum, a plurality of rope plies are pressed closely one against the other and are wound up under the action of the force exerted by the assembly suspended on the rope, this, on the one hand, leading to pronounced mechanical rope stress, for example to rope tears caused by chafing, etc. and moreover also appreciably increasing the risk of corrosion for the individual rope regions lying one against the other. This mechanical stress and corrosion of the rope which progress in course of time ultimately lead to rope breakages regularly occurring, the result of this being that the assembly held on it then slumps downward in an undesirable way onto the bottom of the fermenter tank. The ultimate consequence of this is that the operation of the fermenter tank and therefore of the entire biogas plant has to be stopped and the assembly has to be recovered in a complicated way. This may take place, for example, using divers, but this is highly questionable for safety reasons. In practice, therefore, if such an accident occurs, the fermenter tank is normally emptied and subsequently cleaned because sediments or settling layers are deposited on the fermenter bottom. Moreover, before this work, the tank has to be ventilated in order to remove the biogas still produced, so that this is not harmful to the workers. When such an accident occurs, therefore, a considerable production outage has to be expected, since, after the damage has been rectified, the overall biology has to be reestablished and started again. This usually means, in the event of an accident, a shutdown of the plant of two or three months, which for a biogas plant sometimes may even mean financial failure.

Further, the rope has the disadvantage that it has to be wound up and therefore, in the case of long rope lengths, a relatively large rope drum is also required which usually does not fit through standard servicing orifices or standard servicing shafts.

Furthermore, contaminants, such as, for example, long-fiber material, etc., are also drawn up on the rope and are wound around the rope drum. This then leads to blockages and possibly even to the loss of height adjustment.

A further substantial disadvantage of such a rope winch as a height adjustment device is that the rope is a flexurally slack component which is not dimensionally stable and which is incapable of making the desired guidance stability available when the assembly is being lowered and raised, as a result of which, particularly when the floating layers or foam layers of the fermenter tank are being punctured, lowering problems regularly arise, since these floating or foam layers are often so dense that there is the risk that the assembly itself "floats" to some extent and therefore cannot be lowered quickly and in a functionally reliable manner in the desired way.

Moreover, since the rope is relatively "light", there is the risk that it is sucked up by the blade due to the pull occurring behind the agitator. Consequently, in the event of uncontrolled lowering, in which the assembly remains stuck, for example, in a floating layer, the rope runs the risk of being sucked up and of becoming caught in the blade. As a result of this, not only may the rope tear (thus leading to the disadvantages already described above), but the assembly itself may also be damaged, in that, for example, the blade or blades breaks off or break off at the front; or else the assembly is drawn forward at the top and knocks against its own mast.

If the assembly breaks off and slumps or falls downward, there is also the risk that it penetrates into any heating pipes present, or knocks against the wall and/or other installation parts.

Furthermore, a flexurally slack rope of this type does not enable complete full mixing of the tank to take place.

Clearly, therefore, designing a height adjustment device as a rope winch with rope plies subjected to high mechanical stress, in which the rope drum and the rope capable of being wound on it are also arranged in the fermenter tank inner space and are consequently exposed permanently to a corrosive medium or a corrosive atmosphere, constitutes a considerable potential risk for the permanent functionally reliable operation of the height adjustment device and therefore of the fermenter tank and therefore, in turn, of the entire biogas plant. This risk can be counteracted only by the traction rope being regularly exchanged in the context of servicing work, this obviously entailing an extremely high outlay for the biogas plant operator.

BRIEF SUMMARY OF THE INVENTION

The object of the present invention, therefore, is to make available a biogas plant with a fermenter tank, by means of which assembly adjustment along an assembly carrier in the fermenter tank can be implemented in a simple and functionally reliable way, even over a lengthy period of time.

This object is achieved by means of the features of the main patent claim. Advantageous refinements of this are the subject matter of the subclaims referring back to it.

According to the invention, a biogas plant is proposed, with a fermenter tank in which an assembly carrier is mounted, preferably oriented vertically, an assembly, in particular a submersible motor-driven agitator, being held on the assembly carrier in a height-adjustable manner by means of a height adjustment device. According to the invention, the height adjustment device is formed by a wrap-around drive, the traction means of which is guided around at least two deflection elements spaced apart from one another in the assembly carrier longitudinal direction, at least one of the deflection elements being drivable in rotation by means of a drive device, and the assembly being coupled to the traction means in such a way that it is raised upon rotary actuation of the deflection element in a first direction and lowered upon rotary actuation of the deflection element in a second, opposite direction.

The tie-up of the traction means may take place, in principle, at the same tie-up point on the assembly; however, it is especially preferable to have a tie-up of the two free end regions of the traction means at assembly-side tie-up points spaced apart from one another, for example at assembly-side tie-up points lying more or less opposite one another, as seen in the adjustment direction. Offset tie-up, for example, is also possible.

The particular advantage of this solution according to the invention is that, by means of a wrap-around drive of this type, it can be ensured in a particularly simple way, for example during lowering, that the assembly can be drawn through the fermenter tank-side floating or foam layers, since, by means of such a wrap-around drive, it is ensured in a simple way that, during lowering, a correspondingly downwardly directed tractive force component acts upon the assembly. Moreover, such a wrap-around drive reliably prevents the situation where the traction means can be sucked up by the blade due to the pull which occurs behind an agitator or such like assembly.

Moreover, by means of a set-up of this type, the risk of breakage in respect of the traction means can advantageously be markedly reduced, since a traction means used in this way according to the invention, for example in the form of a traction chain, can be designed to be sufficiently stable so that the traction means, even in a slightly corroded state, still has such sufficient strength to be able to raise and lower an assembly in the medium of the fermenter tank in a functionally reliable and dependable way.

Furthermore, such a traction means does not need to be wound onto a rope drum, and therefore, overall, there is a compact type of construction and the traction means has no regions which are subjected to force and are therefore pressed closely together and one against the other and which are subjected to high mechanical stress. Moreover, because there is no winding of the traction means onto a rope drum, very large height adjustments of an assembly of, for example, well above 6 m can also be implemented in a simple way.

The traction means may, in principle, be designed in various ways, such as, for example, in the manner of a profile belt or toothed belt, if appropriate even as a rope (for example, in conjunction with short maintenance and exchange intervals or times of the rope). Especially preferably, however, the traction means is formed by a stable traction chain, preferably by a multidimensionally movable chain, in particular a link chain or round link chain, or alternatively by a merely one-dimensionally movable articulated chain. A merely one-dimensionally movable articulated chain of this type may be formed, in turn, by a roller chain or a bush chain or bolt chain or such like articulated chains. When a traction chain is used, the rotationally drivable deflection element is then preferably formed by at least one rotatably mounted chain wheel, such as, for example, a chain sprocket, which is in positive engagement with the traction chain. A further essential advantage of such a design of the traction means as a traction chain, particularly as a one-dimensionally movable articulated chain designed, for example, in the manner of a bicycle chain, is that it is heavier than a traction rope and, if appropriate, is dimensionally stable in defined directions and therefore, contrary to a flexurally slack rope, makes available a certain guidance stability which, in conjunction particularly with the lowering of an assembly, is advantageous, since the floating or foam layers which may be formed in the fermenter tank can consequently be punctured more simply and drifting of the assembly can be reliably avoided. Overall, therefore, such a traction chain, particularly in the form of a one-dimensionally movable articulated chain, gives the set-up overall a higher stability.

Thus, by means of the solution according to the invention, a concept, entirely novel in respect of EP 0 894 525 B1 and based on a different functional and operative principle, of a height adjustment device, in conjunction with fermenter tanks of biogas plants, is made available.

It should be expressly mentioned at this juncture that the term "fermenter tank" stands as a generic term for all the tanks of a biogas plant in which an assembly can be mounted in a height-adjustable manner; the term "fermenter tank" is to that extent to be interpreted broadly and comprehensively here.

According to an especially preferred concrete refinement of the idea of the present invention, it is proposed that the individual axes of articulation of the articulated chain are designed to be essentially axially parallel to the axis of rotation of the chain wheel, so that the articulated chain has in the desired way, in the other two directions, a certain dimensional stability and rigidity which contribute to improving the guidance stability of the height adjustment device during the lowering and raising of the assembly.

According to a concrete embodiment according to the invention, it is proposed that the traction means be guided from a tie-up point on the assembly upward in the direction of the vertical axis around a preferably rotationally drivable deflection element and from there downward to at least one lower deflection element, from where the traction means is guided upward again back to the assembly and is tied up there. This ensures that the upper, easily accessible deflection element forms the rotationally driven deflection element and is therefore also easily accessible for servicing and repair work. The lower deflection element may be arranged indirectly or directly on the assembly carrier and may also be formed, for example, by a guide rail or the like. However, a refinement is especially preferred in which the lower deflection element is likewise mounted rotatably, for example is designed as a guide wheel. A refinement is most especially preferred in which, in the event of the traction means being formed by a traction chain, the lower deflection element is also formed by a chain wheel which, similarly to the above-described chain wheel, is in engagement with the traction chain, thus ensuring in a simple way that the traction chain is guided and held positively in a dependable and functionally reliable way along the entire wrap-around drive. Particularly in conjunction with a wrap-around drive of this type, the refinement of the traction means as a one-dimensionally movable articulated chain is also especially advantageous, since this ensures in a simple way that the articulated chain as traction means cannot buckle in the direction of the axis of articulation of the articulated chain, thus ensuring in a simple way that the articulated chain as traction means is held in the wrap-around drive plane provided.

It will be appreciated that the wrap-around drive itself may also have further additional deflection elements or rotatable or non-rotatable deflection elements, such as, for example, chain wheels, this also depending, for example, on the length of the traction means. By means of additional deflection elements of this type, the functional reliability and operating reliability of the wrap-around drive can be ensured in a simple way. Moreover, a tension element formed, for example, by such a deflection element may also be provided, by means of which, for example, the chain tension can be set, this likewise contributing to ensuring the operating reliability of the wrap-around drive and consequently of the height adjustment device.

A wrap-around drive of this type is preferably arranged in the tank inner space of the fermenter tank, the rotationally drivable deflection element or a drive device operatively connected to the latter being actuable from outside the fermenter tank by means of an actuation device. An arrangement of this type in the tank inner space expressly comprises tank configurations in which the height adjustment device according to the invention is arranged in a dome-like region of a servicing shaft.

The deflection elements of the wrap-around drive are secured, spaced apart from one another, to the assembly carrier indirectly or directly, for example via holding and mounting plates and angle pieces, thus ensuring that the wrap-around drive is mounted and arranged in a simple way.

The at least one deflection element of the wrap-around drive may be assigned at least one one-part or multipart guide and/or lead element, for example a lead plate or the like, in such a way that the traction means, in particular a traction chain, such as, for example, a link chain or an articulated chain, is held permanently in engagement with the assigned deflection element, preferably a chain wheel. For this purpose, the at least one one-part or multipart guide and/or lead element is preferably guided around with a defined gap clearance over at least a subregion of the respective deflection element. A guide and/or lead element of this type may, in principle, be designed in various ways. For example, a guide and/or lead element which is upper in the direction of the vertical axis may be designed, in particular designed in multipart form, such that it provides for drawn-up solids an outlet orifice or outlet gap, via which the drawn-up impurities, such as, for example, fibrous substances, can emerge from the region of the wrap-around drive and be separated off. In any event, a refinement is also preferred in which the lead element covers the deflection element, for example a chain wheel, essentially over a large part or else over the entire deflection or engagement region, in order to ensure that, to name only one example, the, for example, desired number of teeth of a chain wheel are also always in engagement with the assigned engagement region of the traction chain or articulated chain.

What all the embodiments have in common is that the rotationally drivable deflection element may be assigned a preferably electrically, hydraulically, pneumatically or manually operable drive device, by means of which the deflection element can be driven in rotation indirectly or directly in a simple way. According to an embodiment which is especially preferred in this respect, there is provision whereby the deflection element is an integral part of a drive shaft which, furthermore, has a drive pinion which cooperates with a gear which drives the drive pinion and therefore the deflection element. Such a set-up makes it possible to have many structural freedoms and, moreover, is highly functionally reliable in daily practice and in attendance. This applies, above all, to the especially preferred case where the gear is an integral part of a hollow shaft arrangement, in which, in a hollow shaft forming, if appropriate, a ceiling wall rotary bearing and/or forming, if appropriate, an integral part of the assembly carrier, a drive shaft is mounted rotatably, which has an engagement region meshing indirectly or directly with the drive pinion. Moreover, this drive shaft is preferably led with a free end out of the fermenter tank. The latter case, above all, makes it possible especially simply and reliably in terms of attendance to provide a drive motor which drives the drive shaft and which can be actuated by an actuation device. In principle, a gear of this type may be designed in many different ways. However, there is especially preferably provision whereby the gear is a worm drive with a worm shaft as drive shaft, the engagement region of which is formed by a worm thread. A worm drive of this type is especially robust and has advantageous self-locking which ensures that set height positions of the assembly can be held in a functionally reliable way.

The invention is explained in more detail below by means of a drawing.

BRIEF DESCRIPTION OF THE SEVERAL VIEWS OF THE DRAWING

In the drawing:

FIG. 5b shows, in the form of a detail, a diagrammatic sectional view through the upper rotary bearing, designed as a hollow shaft arrangement, of the assembly carrier according to FIG. 5a.

DESCRIPTION OF THE INVENTION

Figure 1:
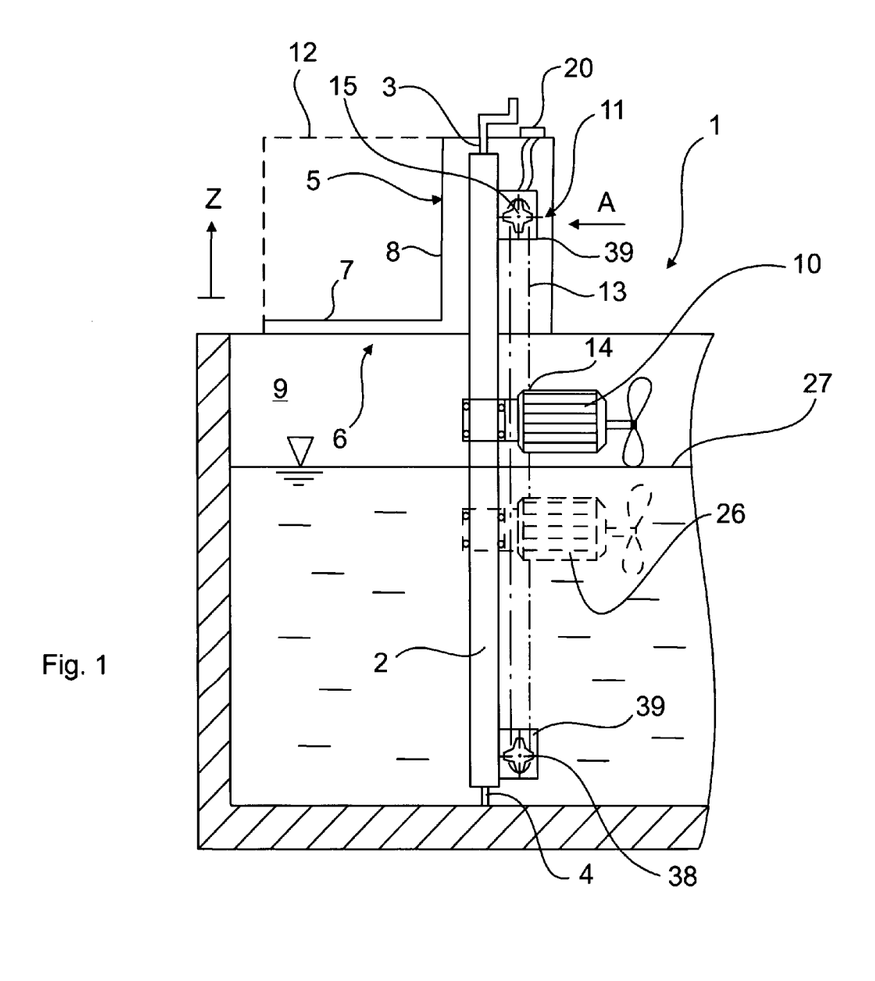
FIG. 1 shows a diagrammatic part view of a fermenter tank of a biogas plant with an assembly carrier mounted vertically therein and with an exemplary embodiment of a height adjustment device according to the invention.

FIG. 1 shows by way of example and diagrammatically a part view of a fermenter tank 1 of a biogas plant, in which an assembly carrier 2 is mounted, oriented vertically.

The assembly carrier 2 may, in principle, be designed in various ways, for example to be round. In the embodiment shown here, the assembly carrier 2 is formed by a square lead pipe of square cross section.

The assembly carrier 2 is rotatable, that is to say it is mounted rotatably about its longitudinal axis in the fermenter tank 1. For this purpose, the assembly carrier 2 has a lower rotary bearing 3 and an upper rotary bearing 4. The lower rotary bearing 3 is formed by the fermenter tank bottom wall, while the upper rotary bearing 4 is formed here, for example, by a ceiling wall of an L-type servicing shaft 5. This L-type servicing shaft 5 covers a ceiling wall-side servicing orifice 6, not illustrated in detail here, of the fermenter tank 1, so that no gases can escape out of the tank inner space 9 into the surroundings. The L-type servicing shaft 5 has, for example, two wall plates 7, 8 which in a servicing situation can be removed from the L-type servicing shaft 5, so that access into the fermenter tank inner space 9 is made possible via the servicing orifice 6.

In a servicing situation, the assembly 10, which is mounted in a height-adjustable manner on the assembly carrier 2 and is formed here, for example, by a submersible motor-driven agitator, can then, by the assembly carrier 2 being pivoted about its longitudinal axis, be pivoted to the left through 180° out of the right-hand position shown in the image plane of FIG. 1, and subsequently, by actuation of the height adjustment device 11, explained in more detail below, can be raised upwardly to an extent such that the assembly 10 is accessible via the servicing orifice 6 or can be displaced outside the fermenter tank 1 through the servicing orifice 6.

Instead of an L-type servicing shaft 5, as shown in FIG. 1, a box-shaped servicing shaft 12 may also be provided, as is depicted merely by dashes in FIG. 1, into which the assembly 10 can be moved for servicing and repair work and which is accessible, for example, via an access door or access flap.

The height adjustment device 11 is formed here by a wrap-around drive, in which an articulated chain 13, movable here, for example, only one-dimensionally, as a traction means or traction chain is guided from a first tie-up point 14 on the assembly 10 upward in the direction z of the vertical axis around a chain wheel 15 and from there downward to a here, for example, lower chain wheel 38 as a lower deflection element which is mounted rotatably on the assembly carrier 2. As may be gathered particularly from FIG. 2, in this embodiment the two chain wheels 15, 38 may be fastened indirectly or, as shown here, directly to the assembly carrier 2 via mounting trestles or mounting plates 39, for example by means of a plurality of screw connections 40. For this purpose, the mounting trestles or mounting plates 39 may preferably be designed to be angled such that the planes of rotation of the chain wheels 15, 38 lie approximately in the longitudinal mid-plane of the assembly carrier 2, so that the assembly 10 itself, oriented approximately centrally, is height-adjustable along the assembly carrier 2. It will be appreciated that the arrangement of the assembly 10 offset with respect to the longitudinal mid-plane of the assembly carrier 2 is, of course, also possible in principle.

Figure 2:
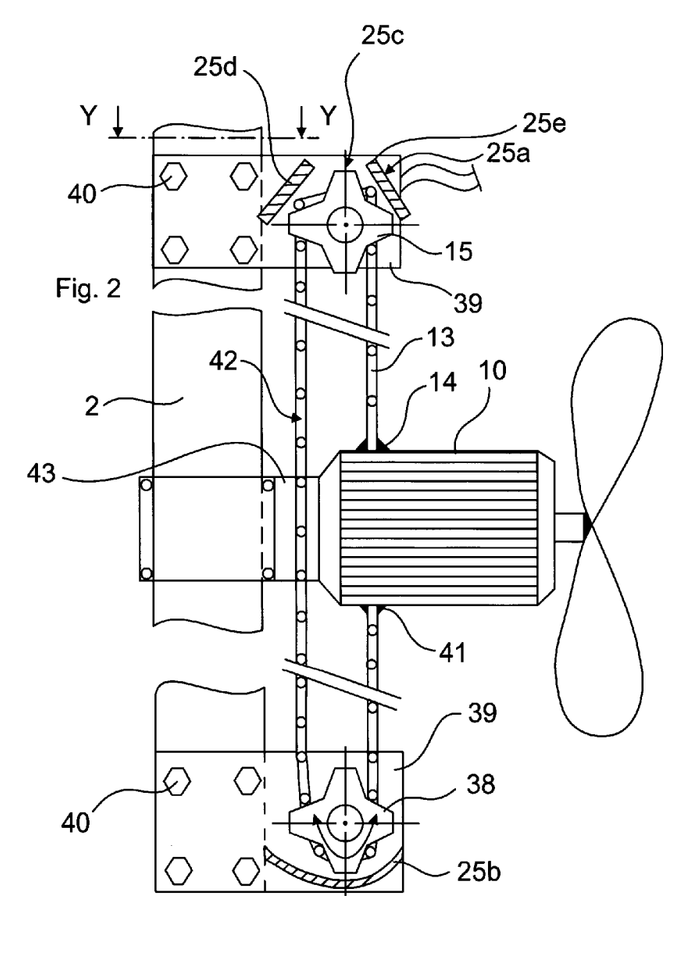
FIG. 2 shows diagrammatically, in the form of a detail, an enlarged illustration of the wrap-around drive of FIG. 1.
Figure 3:
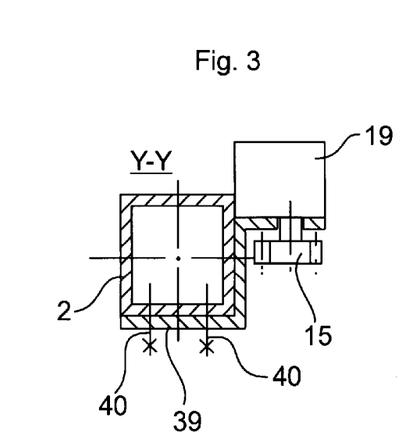
FIG. 3 shows diagrammatically a sectional view along Y-Y of FIG. 2.

The articulated chain 13 is then guided from the lower chain wheel 38 upward again back to the assembly 10 and is tied there with its second free end region to a second tie-up point 41 which here, merely by way of example, lies so as to be spaced apart from and below the first tie-up point 14 of the first free articulated chain end region.

Thus, by means of a set-up of this type, a wrap-around drive is formed, into which the assembly 10 is incorporated in such a way that the assembly 10 can be raised upon rotary actuation of the chain wheel 15 via an electric, pneumatic or hydraulic drive motor 19, flanged, for example, to the upper mounting plane 19 and/or to the assembly carrier 2, in a first direction and can be lowered upon rotary actuation of the chain wheel 15 in a second, opposite direction.

The drive motor 19 is here coupled or operatively connected via piping, hosing or cabling 21 to an actuation device 20 arranged outside the fermenter tank 1.

As is evident particularly from FIG. 2, the free chain region 42 of the articulated chain 13, that is to say that chain subregion, into which the assembly 10 is not incorporated, between the two chain wheels 15 and 38, is guided here, free of obstruction, for example, through a leadthrough 43 formed on the assembly side. This assembly-side leadthrough 43 may be designed, for example, as a slot, gap or such like recess, moreover with or without a guide element, such as, for example, a guide roller or the like. Alternatively to this, however, the chain wheels 15, 38 could also be offset with respect to the longitudinal center of the assembly carrier 2 such that, for example in the case of chain wheel diameters designed to be correspondingly large, the free movement of the free chain region 42 is ensured via the arrangement and/or dimensioning of the chain wheels 15, 38. Alternatively, also, if appropriate, the arrangement of the chain wheels 15 and 38 could also be such that the free chain region 42 runs inside the assembly carrier 2 which is preferably designed as a hollow profile carrier. Furthermore, further deflection elements or tension elements could also be provided, which, for example, supplement and extend the wrap-around drive, shown here, in such a way that chain guidance is designed in the manner of a block and tackle and it is ensured that the free chain region 42 always lies outside the range of movement of the assembly 10.

Moreover, by means of a tension element, the chain tension can be maintained in the desired way, in order to prevent the chain from jumping out. Alternatively or additionally to this, in connection with both chain wheels 15, 38, as illustrated diagrammatically in FIG. 2, there may also be provision, in turn, for providing there lead elements 25 which have a gap clearance with respect to the chain wheel such that the articulated chain 13 is held permanently in engagement connection with the in each case assigned chain wheel 15 or 38.

If, then, as illustrated diagrammatically in FIG. 1, the assembly 10 is to be lowered out of the raised position, shown by unbroken lines, downward into the fermenter tank 1, the drive motor 19 is activated by the actuation device 20 for a predetermined time duration such that said drive motor rotates the chain wheel 15 clockwise until the assembly 10 is lowered into the desired lowered position 26, illustrated here, for example, by dashed lines. When the desired position is reached, the drive motor 19 is stopped and consequently the chain wheel 15 is halted, with the result that the assembly 10 is held reliably in the desired lowered position 26.

It will be appreciated that both the length of the articulated chain 13 and the distance between the two chain wheels 15, 38 are, of course, stipulated such that all the desired height positions of the assembly 10 in the fermenter tank 1 can consequently be assumed.

If the assembly 10 is then to be raised again from the lowered position 26, illustrated by dashes in FIG. 1, into the higher position, illustrated by unbroken lines, once more the drive motor 19 is activated via the actuation device 20, specifically, this time, such that the chain wheel 15 is rotated counterclockwise, as a result of which, in turn, that region of the articulated chain 13 which is tied to the assembly 10 at the first tie-up point 14 and therefore the assembly 10 are drawn upward.

It will be appreciated, further, that the solution according to the invention can, of course, be used with any type of tank or fermenter tank, that is to say, in particular, also with fermenter tanks having a fixed horizontal ceiling wall and with fermenter tanks having a sheet roof or the like.

Provided in each case above the upper rotationally drivable chain wheel 15 and below the lower chain wheel 38 in the direction z of the vertical axis is a lead element 25*a*, 25*b* which has a defined gap clearance in relation to the respective chain wheel 15, 38, in such a way that the articulated chain 13 is held permanently in engagement connection with the chain wheel 15. The lower lead element 25*b* is designed here, for example, to be arcuately curved and is guided, for example, in the form of a lead plate or the like around a large part of the engagement region of the lower chain wheel 38. By contrast, the upper lead element 25*a* is formed here, for example, in two parts by lead jaws 25*d*, 25*e* which are spaced apart from one another and between them form an outlet orifice 25*c* and which here are set obliquely, for example, in a roof-shaped manner, thus ensuring that solids drawn up by the articulated chain 13 can be discharged in a functionally reliable manner via the outlet orifice 25*c* and consequently the risk of blockage in the region of the upper chain wheel 15 is avoided. Such lead elements 25*a*, 25*b* thus ensure a functionally reliable engagement connection between the articulated chain 13 and the respective chain wheel 15, 38 and therefore, in particular, help to prevent the articulated chain 13 from jumping out of the engagement connection with the chain wheel 15 or 38.

Figure 4A:
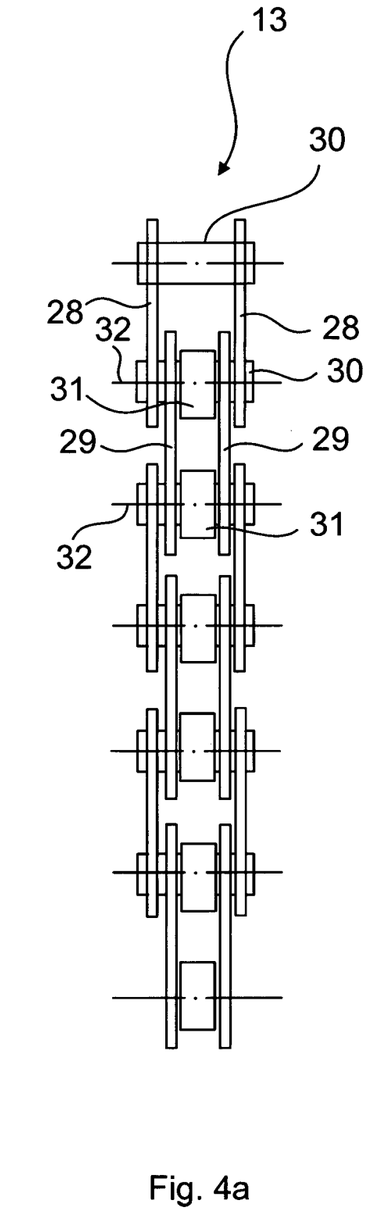
FIG. 4a shows diagrammatically an exemplary illustration of a chain region of an articulated chain designed, for example, as a roller chain.
Figure 4B:
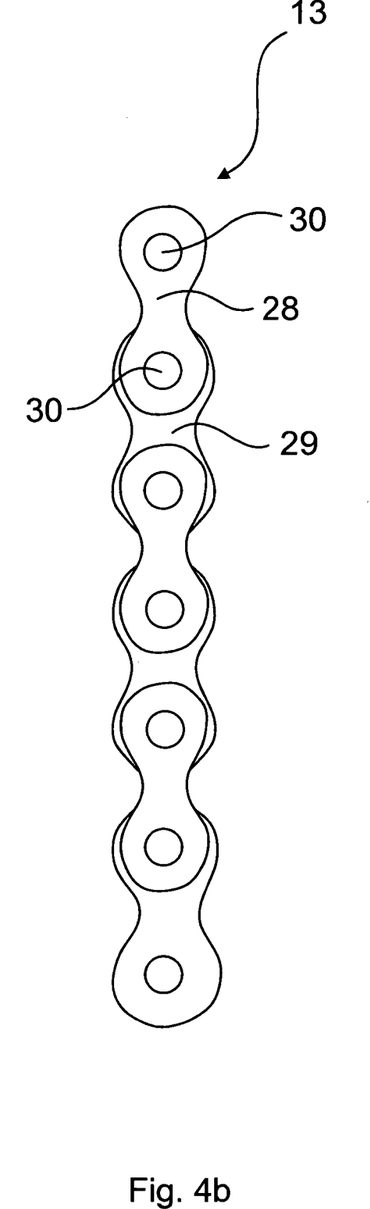
FIG. 4b shows an arrangement, tilted through 90°, of the chain region of FIG. 4a, FIG. 5a shows diagrammatically a further exemplary embodiment, alternative to FIG. 1, with a hollow shaft arrangement.

As may be gathered particularly from FIG. 4*a* and FIG. 4*b*, the traction chain is formed here, for example, by a one-dimensionally movable articulated chain 13, the axes of articulation 32 of which are oriented essentially axially parallel to the axis of rotation of the chain wheel 15, with the result that reliable guidance of the assembly 10 both during raising and during lowering is achieved. In particular, an articulated chain 13 of this type ensures that floating or foam layers 27 possibly present, which are illustrated in FIG. 1 only extremely diagrammatically and by way of example, can be punctured reliably when the assembly 10 is being lowered, since, contrary to an overall flexurally slack rope, the articulated chain 13 does not permit any major shifting movements of the assembly and therefore the puncturing of the floating layer 27 can take place in a more controlled way.

Moreover, such an articulated chain 13 as traction chain makes it possible to stabilize the assembly 10 when the latter is in operation, this having an advantageous effect, for example, upon the agitation result.

As shown in FIGS. 4*a* and 4*b*, the articulated chain is formed here, for example, by outer link plates 28 which are connected to one another via bolts 30 and are spaced apart from one another. Inner link plates 29 are mounted pivotably on the bolts 30, in each case rollers 31 being mounted rotatably on the bolts 30 between the two inner link plates. By means of such an exemplary set-up of an articulated chain 13, advantageous flexural rigidity in the direction of the axes of articulation 32 and to some extent also in the chain longitudinal direction is thus achieved. Articulation is provided to the desired extent around the axes of articulation 32 only.

By means of such an articulated chain 13 as traction chain of a height adjustment device, therefore, desired transverse stabilization and guidance stabilization of an assembly during its height adjustment are made possible, this having a positive effect both on the lowering operation and on the raising operation and, moreover, also resulting in positive effects upon the agitation result by means of the assembly 10 designed, for example, as a submersible motor-driven agitator.

Although the above exemplary embodiments were described in terms of the use of an articulated chain, a multidimensionally, in particular two-dimensionally movable traction chain, for example a link chain, such as, for example, a round link chain, may, of course, be employed and used instead of an articulated chain of this type.

Figure 5A:
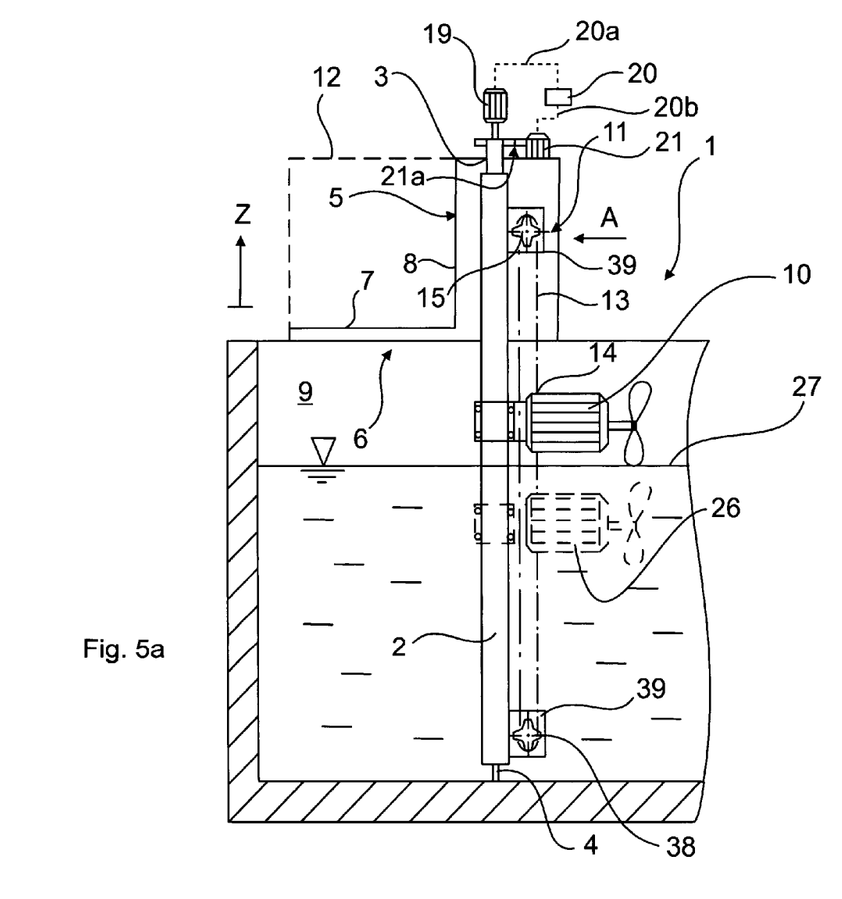
Figure 5B:
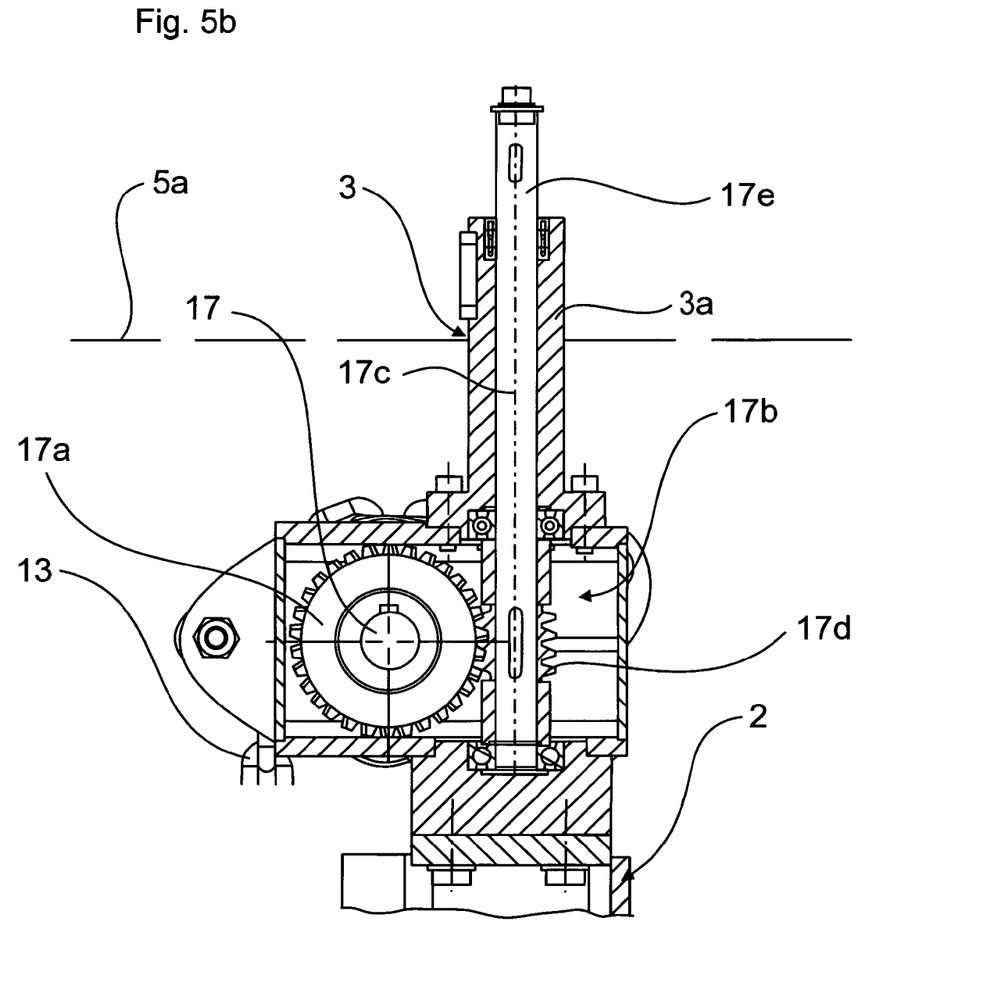

Moreover, FIG. 5*a* shows a refinement, alternative to FIG. 1, in which the chain wheel 15 arranged at the top is an integral part of a drive shaft 17, on which, furthermore, is mounted (FIG. 5*b*) a drive pinion 17*a* which cooperates with a worm drive 17*b* which drives the drive pinion 17*a* and consequently the chain wheel 15. The worm drive 17*b* is an integral part of a hollow shaft arrangement, in which, in a hollow shaft 3*a* forming the ceiling wall rotary bearing 3 and forming an integral part of the assembly carrier 2, a worm shaft 17*c* is mounted rotatably, which has a worm thread 17*d* meshing here directly with the drive pinion 17*a* (the interposition of one or more gear wheels would, of course, also be possible) and which is guided with a free end 17*e* out of the fermenter tank 1, illustrated in FIG. 5*b*, for example, by a ceiling wall 5*a*, depicted by dashes, of the servicing shaft 5. Provided there is a drive motor 19 (FIG. 5*a*) which drives the worm shaft 17*c* and which is illustrated here only extremely diagrammatically and by way of example. This drive motor 19 can be actuated by an actuation device 20 which is likewise arranged outside the fermenter tank 1, for which purpose the drive motor 19 is connected by means of a signal line 20*a*, illustrated by dashes here. It will be appreciated that the drive motor 19, together with the worm shaft 17*c*, is designed such that the worm shaft 17*c* and consequently the drive pinion 17*a* and the chain wheel 15 can be driven in rotation both in one direction and in the other direction.

Furthermore, outside the fermenter tank 1 a further drive motor 21 is arranged (FIG. 5*a*), by means of which the hollow shaft 3*a* connected firmly to the assembly carrier 2 and, consequently, the assembly carrier 2 can be pivoted via a gear arrangement 21*a*, not illustrated any further here. The activation of the drive motor 21 likewise takes place via the actuation device 20 by means of a signal line 20*b*. It should be expressly mentioned at this juncture that the pivoting of the assembly carrier 2 may alternatively also take place manually, for example via a pivoting lever, although this is not illustrated here. The worm shaft 17*c* could likewise also be driven manually, for example by means of a crank handle, although this is not illustrated here.

The invention claimed is:

1. A biogas plant, comprising:
   a fermenter tank having a tank inner space;
   an upper chain wheel;
   a lower chain wheel spaced apart from said upper chain wheel;
   an articulated traction chain mounted vertically within said tank inner space and engaging with said upper and lower chain wheels, said articulated traction chain having axes of articulation which are oriented axially parallel to an axis of rotation of said upper and lower chain wheels;
   a carrier coupled to said articulated traction chain;
   a submersible motor-driven agitator mounted on said carrier;
   an outlet orifice for drawn-up solids positioned above said upper chain wheel, said outlet orifice having two lead jaws spaced apart and set obliquely, said two lead jaws ensuring a functionally reliable engagement between said articulated traction chain and said upper chain wheel; and
   an arcuate lead plate positioned below said lower chained wheel.

2. The biogas plant according to claim 1, wherein said upper chain wheel and said lower chain wheel are secured to said carrier indirectly or directly.

3. The biogas plant according to claim 1, wherein said articulated traction chain is selected from the group consisting of a multi-dimensionally movable chain and a merely one-dimensionally movable articulated chain.

4. The biogas plant according to claim 1, wherein said articulated traction chain is selected from the group consisting of a roller chain, a bush chain and a bolt chain.

5. The biogas plant according to claim 1, wherein said carrier is mounted oriented vertically in said fermenter tank.

6. The biogas plant according to claim 1, wherein:
   said submersible motor-driven agitator has a tie-up point; and
   said articulated traction device is guided from said tie-up point on said submersible motor-driven agitator upward in a direction of a vertical axis around said upper chain wheel and from there downward to said lower chain wheel, from where said articulated traction chain is guided upward again back to said submersible motor-driven agitator and is tied up there.

7. The biogas plant according to claim 6, wherein said lower chain wheel is disposed indirectly or directly on said carrier and is mounted rotatably.

8. The biogas plant according to claim 1, wherein said upper chain wheel is assigned a motor, by means of said motor said upper chain wheel can be driven in rotation indirectly or directly.

9. The biogas plant according to claim 8, wherein said motor is electrically, hydraulically, or pneumatically operatable.

10. The biogas plant according to claim 8, further comprising:
   a gear; and
   a drive shaft, said upper chain wheel is an integral part of said drive shaft, said drive shaft further having a drive pinion which cooperates with said gear which drives said drive pinion and consequently said upper chain wheel.

11. The biogas plant according to claim 10, further comprising:
   a hollow shaft configuration, said gear being an integral part of said hollow shaft configuration, said hollow shaft configuration further having a hollow shaft forming a ceiling wall rotary bearing and/or forming an integral part of said carrier, a further drive shaft mounted rotatably, which has an engagement region meshing indirectly or directly with said drive pinion and which is led with a free end out of said fermenter tank, there being provided said motor which drives said further drive shaft.

12. The biogas plant according to claim 11, wherein said gear is a worm drive with a worm shaft as said further drive shaft, and said engagement region of which is formed by a worm thread.

* * * * *